(12) United States Patent
Harlan et al.

(10) Patent No.: US 8,975,427 B2
(45) Date of Patent: Mar. 10, 2015

(54) SYNTHESIS OF ALKYL CYCLOPENTADIENE COMPOUNDS

(75) Inventors: C. Jeff Harlan, Houston, TX (US); Xianyi Cao, Pearland, TX (US); Francis C. Rix, League City, TX (US)

(73) Assignee: Univation Technologies, LLC, Houston, TX (US)

( * ) Notice: Subject to any disclaimer, the term of this patent is extended or adjusted under 35 U.S.C. 154(b) by 193 days.

(21) Appl. No.: 13/635,766

(22) PCT Filed: Apr. 5, 2011

(86) PCT No.: PCT/US2011/031182
§ 371 (c)(1),
(2), (4) Date: Dec. 13, 2012

(87) PCT Pub. No.: WO2011/136902
PCT Pub. Date: Nov. 3, 2011

(65) Prior Publication Data
US 2013/0085289 A1    Apr. 4, 2013

Related U.S. Application Data

(60) Provisional application No. 61/328,880, filed on Apr. 28, 2010.

(51) Int. Cl.
| | | |
|---|---|---|
| C07F 17/00 | (2006.01) | |
| B01J 31/22 | (2006.01) | |
| C07C 2/54 | (2006.01) | |
| C07C 17/32 | (2006.01) | |
| C07C 1/32 | (2006.01) | |
| C07C 2/86 | (2006.01) | |
| C07C 41/30 | (2006.01) | |

(52) U.S. Cl.
CPC . *C07C 2/54* (2013.01); *C07C 1/326* (2013.01); *C07C 2/861* (2013.01); *C07C 2/868* (2013.01); C07C 2101/10 (2013.01); *C07F 17/00* (2013.01); *B01J 31/2295* (2013.01); *C07C 17/32* (2013.01); *C07C 41/30* (2013.01)
USPC .............. 556/53; 568/631; 570/217; 585/375

(58) Field of Classification Search
CPC ........ C07F 17/00; B01J 31/2295; C07C 2/54; C07C 17/32; C07C 41/30
USPC .............. 585/375; 570/217; 568/631; 556/53
See application file for complete search history.

(56) References Cited

U.S. PATENT DOCUMENTS

| | | | |
|---|---|---|---|
| 4,851,598 A | 7/1989 | Rosenblum et al. | |
| 4,929,782 A | 5/1990 | Venier et al. | |
| 6,175,027 B1 | 1/2001 | Sullivan et al. | |
| 7,196,032 B2 | 3/2007 | Wenzel et al. | |
| 7,323,526 B2 | 1/2008 | Agapiou et al. | |
| 7,504,464 B2 | 3/2009 | Whited et al. | |
| 2010/0022720 A1 | 1/2010 | Sandell et al. | |

FOREIGN PATENT DOCUMENTS

| | | |
|---|---|---|
| EP | 0420436 A1 | 4/1991 |
| JP | 2001097895 A * | 4/2001 |
| WO | WO 00/73248 A1 | 12/2000 |

OTHER PUBLICATIONS

Stille et al., Journal of Organic Chemistry, vol. 52, No, 2, pp. 434-444 (1989).*
Abstract—JP2001097895A; Katsuya, Shimizu et al.; Apr. 10, 2001; Asahi Chemical Corp.
Bukhtiarov et al. "Cathodic Cleavage of C-H Bond. Electrochemical Reduction of Cyclopentadiene, Indene, and Fluorene" Journal of General Chemistry USSR, Consultants Bureau, New York NY vol. 59, No. 2, Feb. 1, 1989, pp. 366-372.
Licht, Andrea I. et al. "CH-Activation Reactions of Substituted Zirconocene Complexes and Their Use in Catalytic Ethylene Polymerization", Journal of Organometallic Chemistry, 2003, 684(1-2), pp. 91-104.
Little, R. Daniel et al. "Intramolecular Diyl Trapping. Total Synthesis of dl-Hirsutene", J. Am. Chem. Soc., 1981, 103(10), pp. 2744-2749.
Newmark, Richard A. et al. "NMR Assignments of Alkylcyclopentadienyl Ligands in Zirconium and Platinum Complexes", Inorganic Chemistry, 1991, 30(4), pp. 853-856.
Sai, M. et al "Copper-Catalyzed Reaction of Alkyl Halides with Cyclopentadienylmagnesium Reagent," Organic Letters (2008), 10(12), 2545-2547.
Stille, John R. et al. "Intramolecular Diels-Alder Reaction of Alpha-beta unsaturated ester dienophiles with cyclopentadienes and the dependance on tether length" Journal of Organic Chemistry vol. 54, Jan. 1, 1989 pp. 434-444.
Stille, John R. et al. "Rearrangement of Bicyclo[2.2.1]Heptane Rings Systems by Titanocene Alkylidene Complexes to Bicyclo[3.2. 0]Heptane Enol Ethers", J. Org. Chem., 1990, 55(3), pp. 843-862.
Stone, Keith J. et al. "An Exceptionally Efficient Method for the Preparation of a Wide Variety of Fulvenes", J. Org. Chem., 1984, 49, pp. 1849-1853.

* cited by examiner

*Primary Examiner* — Porfirio Nazario Gonzalez
(74) *Attorney, Agent, or Firm* — Kristina Leavitt

(57) ABSTRACT

A method of synthesizing an alkyl cyclopentadiene compound is disclosed. The method includes contacting at least one cyclopentadienyl anion source and at least one alkyl group source to form at least one alkyl cyclopentadiene compound. The method further includes extracting the alkyl cyclopentadiene compound with a hydrocarbon solvent. The alkyl cyclopentadiene compound may be converted to a metallocene catalyst compound.

14 Claims, No Drawings

SYNTHESIS OF ALKYL CYCLOPENTADIENE COMPOUNDS

BACKGROUND

Metallocene catalyst compounds are well known olefin polymerization catalysts. While a variety of different techniques may be used to synthesize suitable metallocene catalyst compounds, one technique involves the use of alkyl cyclopentadiene compounds, such as n-propylcyclopentadiene and n-butylcyclopentadiene. Unbridged metallocene catalyst compounds containing at least one n-alkyl cyclopentadienyl ligand (propyl or longer) can show increased productivity over metallocene catalyst compounds that do not contain this group. This increase in productivity has been referred to as the "propyl effect."

One technique for synthesizing n-alkyl cyclopentadienes involves a fulvene intermediate. The fulvene intermediate may be reduced, for example, with $LiAlH_4$ to produced substituted cyclopentadienide which can then be used directly in the synthesis of the metallocene catalyst compound. This technique may be problematic, however, in that it may be difficult to separate the desired cyclopentadienyl compound from the aluminum containing byproducts. An aqueous work-up is often required to achieve the separation which requires isolation of the free cyclopentadiene derivative.

Another technique for synthesizing n-alkyl cyclopentadienes is the reaction of a cyclopentadiene nucleophile with an electrophile, such as an alkyl halide. However, the yield and subsequent purity of the product are highly dependent upon reaction conditions. For example, sodium cyclopentadienide in tetrahydrofuran ("THF") can react readily with alkyl bromides at room temperature, but the reaction typically results in undesirable levels of impurities and yields of the desired product can be low.

N-alkyl cyclopentadienes can be produced more cleanly by reacting alkyl trifluoromethylsulfonate with lithium cyclopentadienide in THF or reacting 1-iodobutane with sodium cyclopentadienide in liquid ammonia. In addition, substituted cyclopentadienes may be produced by reacting sodium cyclopentadienide with alkyl halides in liquid ammonia. However, despite higher yields, these additional techniques require the use of liquid ammonia at low temperature and the use of alkyl trifluoromethanesulfonates which are expensive, air and moisture sensitive, toxic and may not be readily available.

Yet another technique for synthesizing n-alkyl cyclopentadienes involves use a cyclopentadienyl Grignard reagent. For example, cyclopentadienylmagnesium bromide can be reacted with iodomethane to form methylcyclopentadiene. In some instances, an aqueous acid may be used to quench the reaction. However, drawbacks from this procedure include, higher levels of impurities from the aqueous work-up.

Accordingly, there is a need for improved methods of synthesizing alkyl cyclopentadiene compounds.

BRIEF SUMMARY

Disclosed is a method of synthesizing at least one alkyl cyclopentadiene compound, which may comprise contacting at least one cyclopentadienyl anion source and at least one alkyl group source to form at least one alkyl cyclopentadiene compound. The method may further comprise extracting the alkyl cyclopentadiene compound with a hydrocarbon solvent. The alkyl cyclopentadiene compound may be converted to a metallocene catalyst compound.

DETAILED DESCRIPTION

Disclosed herein are methods for the synthesis of one or more alkyl cyclopentadiene compounds from reaction of a cyclopentadienyl anion source and an alkyl group source. In the methods described herein, the reaction conditions have been optimized to provide enhanced purity and improved yields. In addition, the methods may include a non-aqueous workup to isolate and purify the cyclopentadiene compound. As will be described in more detail below, embodiments may further include preparation of metallocene catalyst compounds from the alkyl cyclopentadiene compound.

GENERAL DEFINITIONS

As used herein, the phrase "alkyl cyclopentadiene compound" includes alkyl cyclopentadiene and substituted alkyl derivatives thereof, which may contain heteroatoms. Non-limiting examples of substituent groups on the alkyl cyclopentadiene compound include one or more from the group selected from hydrogen, or linear, branched alkyl radicals and derivatives thereof, including alkenyl radicals, alkynyl radicals, cycloalkyl radicals or aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or any combination thereof. In a preferred embodiment, substituent groups have up to 50 non-hydrogen atoms, preferably from 1 to 30 carbons that can also be substituted with halogens or heteroatoms or the like. Non-limiting examples of alkyl substituents include methyl, ethyl, propyl, butyl, pentyl, hexyl, cyclopentyl, cyclohexyl, benzyl or phenyl groups and the like, including all their isomers, for example tertiary butyl, isopropyl, and the like. Non-limiting examples of substituted alkyl groups include fluoromethyl, fluoroethyl, difluoroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)-silyl, methyl-bis(difluoromethyl)silyl, bromomethyldimethylgermyl and the like; and disubstitiuted boron radicals including dimethylboron for example; and disubstituted pnictogen radicals including dimethylamine, dimethylphosphine, diphenylamine, methylphenylphosphine, chalcogen radicals including methoxy, ethoxy, propoxy, phenoxy, methylsulfide and ethylsulfide. Non-hydrogen substituents on the alky group may include one or more of the following atoms: C, B, Al, Ga, In, Si, Ge, Sn, N, P, As, O, S, or Se, including olefins such as, but not limited to, olefinically unsaturated substituents including vinyl-terminated ligands, for example but-3-enyl, prop-2-enyl, hex-5-enyl and the like. Examples of non-limiting alkyl cyclopentadiene derivatives include those containing substituted alkyl groups such as, for example, fluoromethyl, fluoroethyl, difluoroethyl, iodopropyl, 3-fluoropropyl, 3,3,3-trifluoropropyl, bromohexyl, bromopropyl and bromobutyl, ethoxybenzene, propoxybenzene, ethyltrimethylsilane, and propyltrimethylsilane. Also included are derivatives in which two cyclopentadienyl groups are connected by a bridging group. Non-limiting examples of bridging groups include, alkyl groups, substituted alkyl groups and heteroatom substituted alkyl groups. Useful alkyl cyclopentadiene compounds may comprise any combination of any embodiment described herein.

As used herein, the phrase "alkyl group source" includes compounds capable of providing alkyl groups or substituted alkyl derivatives, which may contain heteroatoms, including, for example, alkyl halides, alkyl sulfonates, and combinations thereof.

As used herein, the phrase "cyclopentadienyl anion source" includes compounds capable of providing cyclopentadienyl anions including, for example, a cyclopentadienyl Grignard reagent, sodium cyclopentadienyl, lithium cyclopentadienyl, potassium cyclopentadienyl, and any combination thereof.

As used herein, the phrase "cyclopentadienyl Grignard reagent" includes reagents having the formula CpMgX, wherein Cp is a cyclopentadienyl ligand or ligand isolobal to cyclopentadienyl, Mg is magnesium, and X is a halogen, such as, for example, fluorine, chlorine, bromine, and iodine. In some embodiments $Cp_2Mg$, magnesocene, may be used alternatively to CpMgX. Any of a variety of different techniques may be used to prepare cyclopentadienyl Grignard reagents suitable for use in embodiments of the present invention. For example, suitable reagents may be prepared by reaction of cyclopentadiene with alkyl Grignard reagents such as MeMgBr, EtMgBr or i-PrMgCl. The cyclopentadienyl Grignard reagent may comprise any combination of two or more reagents described herein.

As used herein, the phrase "metallocene catalyst compound" includes "half sandwich" and "full sandwich" compounds having one or more Cp ligands (as described above) bound to at least one Group 3 to Group 12 metal atom, and one or more leaving group(s) bound to the at least one metal atom. The "metallocene catalyst component" useful in the present invention may comprise any combination of any embodiment described herein.

As used herein, the term "room temperature" generally refers to a temperature in the range of about 18° C. to about 25° C.

As used herein, the term "substituted" means that the group following that term possesses at least one moiety in place of one or more hydrogens in any position, the moieties selected from such groups as halogen radicals (e.g., Cl, F, Br), hydroxyl groups, carbonyl groups, carboxyl groups, amine groups, phosphine groups, alkoxy groups, phenyl groups, naphthyl groups, $C_1$ to $C_{10}$ alkyl groups, $C_2$ to $C_{10}$ alkenyl groups, and combinations thereof. Examples of substituted alkyls and aryls includes, but are not limited to, acyl radicals, alkylamino radicals, alkoxy radicals, aryloxy radicals, alkylthio radicals, dialkylamino radicals, alkoxycarbonyl radicals, aryloxycarbonyl radicals, carbomoyl radicals, alkyl- and dialkyl-carbamoyl radicals, acyloxy radicals, acylamino radicals, arylamino radicals, and combinations thereof.

As used herein, in reference to Periodic Table "Groups" of Elements, the "new" numbering scheme for the Period Table Groups are used as in the CRC HANDBOOK OF CHEMISTRY AND PHYSICS (David R. Lide ed., CRC Press $81^{st}$ ed. 2000).

Synthesis of Alkyl Cyclopentadiene Compounds

Described herein is the synthesis of one or more alkyl cyclopentadiene compounds from a reaction of components comprising a cyclopentadienyl anion source and an alkyl group source. Non-limiting examples of a suitable alkyl group source include alkyl halides and alkyl sulfonates. The alkyl group source may include, for example, a $C_1$ to $C_{30}$ alkyl group or substituted alkyl derivative thereof. In some embodiments, the alkyl group source may include a $C_3$ to $C_{30}$ alkyl group and, preferably, a $C_3$ to $C_{12}$ alkyl group. In some embodiments, the alkyl group source includes a $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkyl group.

Suitable alkyl halides may include, for example, those of the general formula RX, wherein R is a $C_1$ to $C_{30}$ alkyl group and X is a halogen, such as, for example, fluorine, chlorine, bromine, and iodine. In some embodiments, R is a $C_3$ to $C_{30}$ alkyl group and, preferably, a $C_3$ to $C_{12}$ alkyl group. In some embodiments, R is a $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkyl group. Non-limiting examples of suitable alkyl halides include iodopentane, bromohexane, bromoheptane, bromooctane, bromodecane, and bromododecane. Additionally, the alkyl halide may be substituted in that the alkyl halide contains at least one moiety in place of one or more hydrogens in any position. For example, one or more hydrogens may be replaced with a halogen radical, such as fluorine, chlorine, bromine, or iodine. Non-limiting examples include, trifluoropropyl halide, 1-bromo-3 fluoro propane, 1-bromo-3,3,3-trifluoropropane, 1-bromo-4-fluorobutane, (3-bromopropoxy)benzene, (2-bromoethoxy)benzene chloromethylmethylether, bromomethylmethylether, 2-bromo-N,N-dimethylethanamine, 1,4-dibromobutane. Useful alkyl halides may comprise any combination of any embodiments described herein.

Suitable alkyl sulfonates may include, for example, those of the general formula $R_1SO_3R_2$, wherein $R_1SO_3$ is a mesyl, tosyl, triflate, or other suitable sulfonate leaving group, and $R_2$ is a $C_1$ to $C_{30}$ alkyl group. In some embodiment, $R_2$ is a $C_3$ to $C_{30}$ alkyl group and, preferably, a $C_3$ to $C_{12}$ alkyl group. In some embodiments, $R_2$ is a $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkyl group. Non-limiting examples of suitable alkyl sulfonates include, for example, alkyl mesylates, alkyl tosylates, and alkyl triflates. Additionally, the alkyl sulfonate may be substituted in that the alkyl group may contain at least one moiety in place of one or more hydrogens in any position. Useful alkyl sulfonates may comprise any combination of any embodiment described herein.

The components of the reaction may be present in a suitable solvent, such as, for example, THF (tetrahydrofuran). Non-limiting examples of other suitable solvents include dichloromethane, pentane, cyclopentane, hexane, cyclohexane, benzene, toluene, diethyl ether, di-n-butyl ether, 1,4-dioxane, and combinations thereof.

The alkyl cyclopentadiene compound may include, for example, a $C_1$ to $C_{30}$ alkyl group, a $C_3$ to $C_{30}$ alkyl group, or a $C_3$ to $C_{12}$ alkyl group. In some embodiments, the alkyl cyclopentadiene compound includes a $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkyl group. As discussed above, the alkyl group may be substituted in certain embodiments. For example, the alkyl group may be substituted with at least one heteroatom or at least one heteroatom-containing group. The alkyl group may be substituted with a halogen, such as fluorine, chlorine, bromine or iodine. The alkyl group may be substituted with an oxygen atom forming an alkyoxy or aryloxy group. The alkyl group may be substituted with a group containing one or more of the following atoms: B, Al, Ga, In, Si, Ge, Sn, N, P, As, O, S, or Se. Non-limiting examples of specific alkyl cyclopentadiene compounds include n-propylcyclopentadiene n-butylcyclopentadiene n-pentylcyclopentadiene, n-hexylcyclopentadiene, n-heptylcyclopentadiene, n-octylcyclopentadiene, n-nonylcyclopentadiene, n-decylcyclopentadiene, n-dodecyclopentadiene, 3-chloropropylcyclopentadiene, 3-phenoxypropylcyclopentadiene, and 2-phenoxyethylcyclopentadiene. In some embodiment, the alkyl cyclopentadiene may comprise an n-alkyl cyclopentadiene or a mixture of n-alkyl cyclopentadienes, such as a mixture of 1-alkyl cyclopentadiene and 2-alkyl cyclopentadiene.

Without being limited by theory, it is believed that equimolar amounts of the cyclopentadienyl anion source (e.g., cyclopentadienyl Grignard reagent) and the alkyl group source (e.g., alkyl halide) require long reaction times to get both components to completely react. In addition, it is believed that long reaction times will result in the buildup of undesirable impurities (e.g., dimers of the alkyl cyclopentadiene compounds) in the reaction mixture. Accordingly, to ensure that the alkyl group source is consumed in a timely fashion, the amount of the alkyl group source may be reduced relative to the amount of the cyclopentadienyl anion source in accordance with the methods described herein. Advantageously, present embodiments may have a mole ratio of the alkyl group source to the cyclopentadienyl anion source that is less than 1:1. By way of example, the mole ratio may be within the range of from about 0.5:1 to about 0.9:1, or about 0.7:1 to about 0.8:1. The mole ratio may be about 0.5:1, about 0.6:1, about 0.7:1, about 0.8:1, or about 0.9:1. In an embodiment, the mole ratio of the alkyl group source to the cyclopentadienyl anion source may be about 0.75:1. It should be understood that the present invention also encompasses embodiments with equimolar amounts of the alkyl group source and the cyclopentadienyl anion source and embodiments with a mole ratio of the alkyl group source to the cyclopentadienyl anion source that is greater than 1. For example, the mole ratio may be within the range of about 1.5:1 to about 1.1:1.

In general, the reaction time is the time that the components are held at about the reaction temperature. In accordance with embodiments of the present invention, the reaction may occur for a time sufficient to form the desired alkyl cyclopentadiene compound(s) without the buildup of undesired impurities. For example, the reaction time may be in the range of from about 1 hour to about 10 hours, or about 4 to about 7 hours, or about 5 to about 6 hours. In some embodiments the reaction time may be about 1 hour, about 2 hours, about 3 hours, about 4 hours, about 5 hours, about 6 hours, about 7 hours, about 8 hours, about 9 hours, or about 10 hours. Those of ordinary skill in the art, with the benefit of this disclosure, should understand that the reaction times outside these ranges may also be suitable for certain embodiments. In addition, it should be understood that the reaction time for a particular application may vary depending upon a number of factors, including the particular reactants, the reaction temperature, and the concentration of reactants, among others.

A reaction temperature may be selected, for example, that allows the reaction to proceed at a desired rate without undesired vaporization of the solvent. The reaction may occur, for example, at a temperature ranging from about 25° C. to about 65° C., or about 50° C. to about 65° C. and, or from about 60° C. to about 65° C. These temperature ranges may be particularly suitable for a particular solvent, such as, for example, THF. However, other temperatures outside the listed ranges may be suitable depending on, for example, the boiling point of the particular solvent that was selected.

Work-Up of the Alkyl Cyclopentadiene Compounds

Embodiments of the present invention further may include working up the reaction mixture to, for example, isolate and purify alkyl cyclopentadiene compound(s). In accordance with present embodiments, the work up may include one or more of the following steps: removal of the solvent (e.g., THF) from the reaction mixture, extraction of the alkyl cyclopentadiene compound(s) from the reaction mixture with a hydrocarbon solvent (e.g., pentane), filtration of solid byproducts from the reaction mixture, removal of the hydrocarbon solvent. For example, the work up may include removal of the solvent, THF, from the reaction mixture by vacuum followed by addition of a hydrocarbon solvent (e.g., pentane). In general, the desired products should dissolve in the hydrocarbon solvent from which the solid byproducts may then be filtered to isolate the liquid containing the cyclopentadiene derivatives. From this isolated liquid, the hydrocarbon solvent may then be removed by vacuum, with the residue containing the desired alkyl cyclopentadiene compound(s). In an embodiment, the filtered solids may be washed by additional hydrocarbon solvent and filtered. The hydrocarbon solvent from the wash may be placed under vacuum to remove the solvent and yield additional quantities of the alkyl cyclopentadiene compound(s). Depending on the boiling points of the specific cyclopentadiene derivative(s) and the hydrocarbon solvent used to extract it away from the solid byproducts, the work up may further include, for example, a distillation step to separate the cyclopentadiene derivative(s) from the hydrocarbon solvent. Accordingly, the alkyl cyclopentadiene compound(s) may be isolated without an aqueous work-up in accordance with embodiments of the present invention.

Without being limited by theory, it is believed that embodiments of the workup will yield alkyl cyclopentadiene compound(s) of high enough purity to be used in further reactions, such as in the synthesis of metallocene catalyst compounds. In addition, it is believed that embodiments of the work up should give higher yields of the alkyl cyclopentadiene compounds for the longer chain derivatives (e.g., 5, 6, 7 or more carbons) as opposed to shorter chain derivatives (e.g., fewer than 5 carbons) due to, for example, loss of the more volatile shorter chain derivatives during solvent removal. This is an advantage for the longer chain derivatives because they are more difficult to purify via distillation.

As previously mentioned, the alkyl cyclopentadiene compounds may be extracted from the reaction mixture with a hydrocarbon solvent. This extraction may include, for example, addition of the hydrocarbon solvent to the reaction mixture to dissolve the alkyl cyclopentadiene compounds. Non-limiting examples of suitable hydrocarbon solvents include pentane, cyclopentane, hexane, isohexane, cyclohexane, benzene, and toluene. Useful hydrocarbon solvents may comprise any combination of any embodiment described herein.

Synthesis of Metallocene Catalyst Compounds

Embodiments of the present invention further may include synthesis of metallocene catalyst compounds by reaction of the alkyl cyclopentadiene compound(s) with additional reactant(s). Any suitable technique for preparation of the metallocene catalyst compounds from the alkyl cyclopentadiene compounds may be used in accordance with embodiments of the present invention. One method of metallocene synthesis includes the reaction of the alkyl cyclopentadiene compound with a base to form a cyclopentadienide anion which can then be reacted with a metal-containing compound to form the metallocene catalyst compound. In one embodiment, the alkyl cyclopentadiene compound may be reacted with n-butyl lithium to form the Li cyclopentadienide derivative. Two equivalents of this Li cyclopentadienide derivative may then be reacted with one equivalent of zirconium tetrachloride in an appropriate solvent to form the metallocene catalyst compounds. Metallocene catalyst compounds containing two different cyclopentadiene groups may be made by reacting one equivalent of the Li cyclopentadienide derivative with one equivalent of a cyclopentadienyl zirconium trichloride derivative in an appropriate solvent. Mono cyclopentadienyl zirconium or hafnium trichloride derivatives may be made by first converting the cyclopentadiene derivative compound to a trialkylsilanecyclopentadiene derivative or trialkyltincyclopentadiene derivative and reacting it further with zirconium or hafnium tetrachloride. In one embodiment, the Li cyclopentadienide derivative may be treated with chlorotrimethylsilane to form the trialkylsilane cyclopentadiene derivative, which is then reacted with hafnium tetrachloride to form the monocyclopentadiene hafnium trichloride derivative. It should be understood that other suitable techniques for preparation of the metallocene catalyst compounds may be used.

As described above, the metallocene catalyst compound that may be prepared in accordance with embodiments of the present invention include "half sandwich" (mono cyclopentadienyl) and "full sandwich" (bis cyclopentadienyl) compounds having one or more Cp ligands (as described above) bound to at least one Group 3 to Group 12 metal atom, and one or more leaving group(s) bound to the at least one metal atom.

The metal atom "M" of the metallocene catalyst compound may be selected from the group consisting of Groups 3 through 12 atoms and lanthanide Group atoms in one embodiment; and selected from the group consisting of Groups 3 through 10 atoms in another embodiment, and selected from the group consisting of Sc, Ti, Zr, Hf, V, Nb, Ta, Mn, Re, Fe, Ru, Os, Co, Rh, Ir, and Ni in another embodiment; and selected from the group consisting of Groups 4, 5 and 6 atoms in another embodiment, and Ti, Zr, Hf atoms in another embodiment, and Zr in another embodiment. The oxidation state of the metal atom "M" may range from 0 to +7 in one embodiment, in another embodiment, is +1, +2, +3, +4 or +5 and in another embodiment is +2, +3 or +4 and in other embodiment is +4. The groups bound the metal atom "M" are such that the compounds described below in the formulas and structures are electrically neutral, unless otherwise indicated. The Cp ligand(s) form at least one chemical bond with the metal atom M to form the "metallocene catalyst compound." The Cp ligands are distinct from the leaving groups bound to the catalyst compound in that they are not highly susceptible to substitution/abstraction reactions.

The one or more metallocene catalyst components may be represented by formula (I):

$$Cp_A Cp_B MX_n \quad (I)$$

wherein M is as described above; each X is chemically bonded to M; each Cp group is chemically bonded to M; and n is 0 or an integer from 1 to 4, and either 1 or 2 in an embodiment.

The ligands represented by $Cp_A$ and $Cp_B$ in formula (I) may be the same or different cyclopentadienyl ligands or one may independently be a ligand isolobal to cyclopentadienyl, which may contain heteroatoms, either or both of the cyclopentadienyl ligands may be substituted by a group R. In one embodiment, $Cp_A$ is a substituted cyclopentadienyl ligand and $Cp_B$ is independently selected from the group consisting of cyclopentadienyl, indenyl, tetrahydroindenyl, fluorenyl, and substituted derivatives of each.

$Cp_A$ may be substituted with a single R group and $Cp_B$ of formula (I) may be unsubstituted or substituted with any one or combination of substituent groups R. Non-limiting examples of substituent groups R as used in structure (I) include groups selected from the group consisting of hydrogen radicals, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof.

Other non-limiting examples of alkyl substituents R associated with formula (I) through (IV) include methyl, ethyl, propyl, butyl, pentyl, hexyl, cyclopentyl, cyclohexyl, benzyl, phenyl, methylphenyl, and tert-butylphenyl groups, including all their isomers, for example tertiary-butyl, and isopropyl. Other possible radicals include substituted alkyls and aryls such as, for example, fluoromethyl, fluorethyl, difluorethyl, iodopropyl, bromobutyl, bromohexyl, chlorobenzyl and hydrocarbyl substituted organometalloid radicals including trimethylsilyl, trimethylgermyl, and methyldiethylsilyl; and halocarbyl-substituted organometalloid radicals including tris(trifluoromethyl)silyl, methylbis(difluoromethyl)silyl, and bromomethyldimethylgermyl; and disubstituted boron radicals including dimethylboron for example; and disubstituted Group 15 radicals including dimethylamine, dimethylphosphine, diphenylamine, methylphenylphosphine, Group 16 radicals including methoxy, ethoxy, propoxy, phenoxy, methylsulfide and ethylsulfide. Other substituents R include olefins such as but not limited to olefinically unsaturated substituents including vinyl-terminated ligands, for example 3-butenyl, 2-propenyl, and 5-hexenyl. In one embodiment, at least two R groups, two adjacent R groups in one embodiment, are joined to form a ring structure having from 3 to 30 atoms selected from the group consisting of carbon, nitrogen, oxygen, phosphorous, silicon, germanium, aluminum, boron and combinations thereof. Also, a substituent group R group may form a bonding association or other type of interaction with the element M.

Each X in the formula (I) above may be independently selected from the group consisting of: halogen ions, alkyl groups, heteroatom containing alkyl groups, aryl groups, heteroatom containing aryl groups, aryloxy groups, fluorine containing aryloxy groups, and dialkyl amido groups. In a particular embodiment X is chloride, in another embodiment X is fluoride, in another embodiment X is methyl, in another embodiment X is benzyl.

In some embodiments, the metallocene catalyst component includes those of formula (II) where $Cp_A$ and $Cp_B$ are bridged to each other by at least one bridging group, (A), such that the structure is represented by formula (II):

$$Cp_A(A)Cp_B MX_n \quad (II)$$

These bridged compounds represented by formula (II) are known as "bridged metallocenes." $Cp_A$, $Cp_B$, M, X and n in structure (II) are as defined above for formula (I); and wherein each Cp ligand is chemically bonded to M, and (A) is chemically bonded to each Cp. Non-limiting examples of bridging group (A) include divalent hydrocarbon groups, divalent hydrocarbon groups containing at least one Group 13 to 16 atom, such as but not limited to at least one of a carbon, oxygen, nitrogen, silicon, aluminum, boron, germanium and tin atom and combinations thereof; wherein the heteroatom may also be $C_1$ to $C_{12}$ alkyl or aryl substituted to satisfy neutral valency. The bridging group (A) may also contain substituent groups R as defined above (for formula (I)) including halogen radicals and iron.

Bridging group (A) may also be cyclic, comprising, for example, 4 to 10 ring members, or 5 to 7 ring members. The ring members may be selected from the elements mentioned above in one embodiment and from one or more of B, C, Si, Ge, N and O in another embodiment. Non-limiting examples of ring structures which may be present as or part of the bridging moiety are cyclobutylidene, cyclopentylidene, cyclohexylidene, cycloheptylidene, cyclooctylidene and the corresponding rings where one or two carbon atoms are replaced by at least one of Si, Ge, N and O. The bonding arrangement between the ring and the Cp groups may be either cis-, trans-, or a combination.

The ligands $Cp_A$ and $Cp_B$ of formulae (I) and (II) are different from each other in one embodiment, and the same in another embodiment.

In some embodiments, the metallocene catalyst components include bridged mono-ligand metallocene compounds (e.g. mono cyclopentadienyl catalyst components). The Group Q may or may not be bonded or interacting with the metal M. The metallocene catalyst component may be a bridged "half-sandwich" metallocene, such as those described in U.S. Pat. No. 5,055,438, and may be represented by the formula (III):

$$Cp_A(A)QMX_n \quad (III)$$

wherein $Cp_A$ is defined above and is bound to M; (A) is a bridging group bonded to Q and $Cp_A$; and wherein an atom from the Q group is bonded to M; and n is 0 or an integer from 1 to 3; 1 or 2 in another embodiment and in another embodiment n is 3. In formula (III) above, $Cp_A$, (A) and Q may form a fused ring system. The X groups and n of formula (III) are as defined above in formula (I) and (II).

In formula (III), Q may be a heteroatom-containing ligand in which the bonding atom (the atom that is bonded with the metal M) is selected from the group consisting of Group 14 atoms, Group 15 atoms, and Group 16 atoms in one embodiment, and selected from the group consisting of nitrogen, phosphorus, oxygen or sulfur atom in another embodiment, and nitrogen and oxygen in another embodiment. Non-limiting examples of Q groups include alkylamines, dialkyl amines, arylamines, diarylamines, alkylphosphines, dialkylphosphines, arylphosphines, diarylphosphines, mercapto compounds, thioethers, alkoxy compounds, carboxylates (e.g., pivalate), carbamates, phosphoyl, phosphinimine, pyrrolyl, pyrozolyl, carbazolyl, borabenzene or other compounds comprising Group 15 and Group 16 atoms capable of bonding with M.

In some embodiments, the metallocene component may have two metal centers bridged by a connecting group (A) that connects two cyclopentadienyl groups each of which is chemically bonded to a separate metal as represented by formula (IV):

$$Cp_{B1}M_1X_nCp_{A1}(A)Cp_{A2}Cp_{B2}M_2X_n \quad (IV)$$

In this embodiment $M_1$ may either be the same or different metal than $M_2$ and $Cp_{A1}$ may be the same or different than $Cp_{A2}$ and $Cp_{B1}$ may either be the same or different than $Cp_{B2}$. The cyclopentadienyl groups ($Cp_{A1}$, $Cp_{A2}$, $Cp_{B1}$, $Cp_{B2}$), metals ($M_1$ and $M_2$), leaving groups ($X_n$) and bridging group (A) are as described above.

It is contemplated that the metallocene catalyst's components described above include their structural or optical or enantiomeric isomers (racemic mixture), and may be a pure enantiomer in one embodiment.

As used herein, a single, bridged, asymmetrically substituted metallocene catalyst component having a racemic and/or meso isomer does not, itself, constitute at least two different bridged, metallocene catalyst components. In an embodiment, the metallocenes described herein are in their racemic form.

EXAMPLES

To facilitate a better understanding of the present invention, the following examples of certain aspects of some embodiments are given. In no way should the following examples be read to limit, or define, the entire scope of the invention.

General Procedures

All of the following examples were performed under an atmosphere of dry nitrogen in a glovebox. Anhydrous solvents were purchased from Aldrich, degassed prior to use, and stored over activated alumina. The reactions were performed in round bottom flasks, and filtrations were done with fritted glass funnels. Heating and stirring were done on a magnetic stirrer hotplate equipped with an Optitherm® reaction block. Teflon-coated stir bars were used in the flasks.

$^1$H NMR Spectra were obtained for the alkyl cyclopentadiene compounds prepared in Examples 1-10. In examples 1-6, the isolated n-alkyl cyclopentadienes comprise an approximately 1:1 mixture of the 1-alkyl-cyclopentadiene and 2-alkyl-cyclopentadiene isomers. A value of 2 has been assigned to the most upfield methylene resonances of the 5 position of cyclopentadiene ring (δ 2.69). The methylene resonances of the 5 position of cyclopentadiene ring of the other isomer is slightly downfield (δ 2.79). The ratio of these two peaks determines the ratio of the isomers. Many of the other resonances are either partially or fully overlapping. The $^1$HNMR Spectra of the heteroatom substituted cyclopentadienes, examples 7-10, were also recorded and a value of 2 was arbitrarily assigned to one of the methylene resonances of the 5 position of cyclopentadiene ring. $^1$H NMR Spectra were also obtained for the bis(n-alkylcyclopentadienyl)zirconiumdichlorides that were prepared in Examples 10-16 and the (tetramethylcyclopentadienyl)(n-alkylcyclopentadienyl)zirconiumdichlorides that were prepared in Examples 16-19. All data is taken in $C_6D_6$ at 500 MHz and room temperature unless otherwise specified.

Example 1

Synthesis of $CpC_5H_{11}$

To a stirring solution of CpMgCl (50.0 ml, 1.00 M/THF, 50.0 mmol) was added 1-iodopentane (8.4 g, 42 mmol). The solution was heated at 60° C. for a several minutes. After removing it from the heat, the solution continued to boil gently for about 5 minutes. Next, the solution was stirred for 3 hours at room temperature and then heated to 60° C. for 1 hour. The THF was removed from the solution under vacuum, and the resulting material was extracted with pentane (60 ml) with the liquid extract isolated by filtration. The isolated liquid was transferred to a new flask. The remaining solid was washed with pentane (20 ml) and filtered. The isolated liquid from the pentane extraction and the liquid from the wash were combined and placed under vacuum to remove the pentane and yield the product, a light yellow liquid. Yield=4.0 grams (69% based on 1-iodopentane).

$^1$H NMR Spectra were obtained for the alkyl cyclopentadiene compounds prepared in this example. $^1$H NMR (THF-$d_8$) δ 6.36 (m, 0.78H), 6.31 (m, 1.58H), 6.13 (m, 0.87H), 6.07 (m, 0.84H), 5.92 (m, 0.73H), 2.85 (m, 1.69H), 2.79 (m, 2.00H), 2.35 (m, 1.98H), 2.30 (m, 1.67H), 1.50 (m, 4.00H), 1.30 (m, 10.38H), 0.86 (m, 6.67H).

Example 2

Synthesis of $CpC_6H_{13}$

Sample 1. To a stirring solution of CpMgCl (100 ml, 1.1 M/THF, 110 mmol) was added 1-bromohexane (13.6 g, 82.4 mmol). The solution was heated at 60° C. for 4.5 hours. THF was then removed under vacuum, and the resulting material was extracted with pentane (100 ml) with the liquid extract isolated by filtration. The isolated liquid was transferred to a new flask. The remaining solid was washed with pentane (30 ml) and filtered. The isolated liquid from the pentane extraction and the liquid from the wash were combined and placed under vacuum (1.5 hours) to remove the pentane and yield the product. Yield=8.11 g (65.5% based on 1-bromohexane).

Sample 2. To a stirring solution of CpMgCl (170 ml, 1.30 M/THF, 221 mmol) was added 1-bromohexane (27.2 g, 165 mmol). The solution was heated at 60° C. for 5 hours. The THF was then removed under vacuum, and the resulting material was extracted with pentane (200 ml) with the liquid extract isolated by filtration. The isolated liquid was transferred to a new flask. The remaining solid was washed with pentane (60 ml) and filtered. The isolated liquid from the pentane extraction and the liquid from the wash were combined and placed under vacuum to remove the pentane and yield the product. Yield=22.0 g (88.7% based on 1-bromohexane).

Sample 3. To a stirring solution of CpMgCl (220 ml, 1.0 M/THF, 220 mmol) was added 1-bromohexane (27.2 g, 165 mmol). The solution was heated at 60° C. for 4.5 hours. The THF was then removed under vacuum, and the resulting material was extracted with pentane (200 ml) with the liquid extract isolated by filtration. The isolated liquid was transferred to a new flask. The remaining solid was washed with pentane (60 ml) and filtered. The isolated liquid from the pentane extraction and the liquid from the wash were combined and placed under vacuum to remove the pentane and yield the product. Yield=21.04 g (85% based on 1-bromohexane).

$^1$H NMR Spectra were obtained for representative alkyl cyclopentadiene compounds prepared in this example. $^1$H NMR δ 6.47 (m, 1.87H), 6.35 (m, 0.99H), 6.22 (m, 0.92H), 6.18 (m, 0.87H), 5.97 (m, 1.01H), 2.79 (m, 2.41H), 2.69 (m, 2.00H), 2.33-2.28 (m, 4.82H), 1.53 (m, 2.97H), 1.46 (m, 2.81H), 1.23 (m, 17.77H), 0.878 (m, 8.68H).

Example 3

Synthesis of $CpC_7H_{15}$

To a stirring solution of CpMgCl (50.0 ml, 1.00 M/THF, 50.0 mmol) was added 1-bromoheptane (6.72 g, 37.5 mmol). The solution was heated at 60° C. for 9 hours. The THF was then removed under vacuum, and the resulting material was extracted with pentane (40 ml) with the liquid extract isolated by filtration. The isolated liquid was transferred to a new flask. The isolated liquid was placed under vacuum for 1 hour to remove the pentane and yield the product. Yield=4.22 g (68.6% based on 1-bromoheptane).

$^1$H NMR Spectra were obtained for the alkyl cyclopentadiene compounds prepared in this example. $^1$H NMR δ 6.47 (m, 2.02H), 6.35 (m, 1.12H), 6.22 (m, 0.94H), 6.18 (m, 0.92H), 5.97 (m, 1.15H), 2.79 (m, 2.65H), 2.69 (m, 2.00H), 2.33-2.28 (m, 4.69H), 1.53 (m, 3.04H), 1.46 (m, 2.59H), 1.23 (m, 23.26H), 0.878 (m, 9.0H).

Example 4

Synthesis of $CpC_8H_{17}$

Sample 1. To a stirring solution of CpMgCl (75 ml, 1.00 M/THF, 75 mmol) was added 1-bromooctane (10.87 g, 56 mmol). The solution was heated at 60° C. for 5 hours. The THF was then removed under vacuum, and the resulting material was extracted with pentane (100 ml) with the liquid extract isolated by filtration. The isolated liquid was transferred to a new flask. The remaining solid was washed with pentane (30 ml) and filtered. The isolated liquid from the pentane extraction and the liquid from the wash were combined and placed under vacuum (1.5 hours) to remove the pentane and yield the product. Yield=8.7 g (86.7% based on 1-bromooctane).

Sample 2. To a stirring solution of CpMgCl (96.0 ml, 1.30 M/THF, 125 mmol) was added 1-bromooctane (18.0 g, 93.2 mmol). The solution was heated at 60° C. for 5 hours. The THF was then removed under vacuum, and the resulting material was extracted with pentane (100 ml) with the liquid extract isolated by filtration. The isolated liquid was transferred to a new flask. The remaining solid was washed with pentane (40 ml) and filtered. The isolated liquid from the pentane extraction and the liquid from the wash were combined and placed under vacuum to remove the pentane and yield the product. Yield=15.3 g (92.1% based on 1-bromooctane).

Sample 3. To a stirring solution of CpMgCl (200 ml, 1.0 M/THF, 200 mmol) was added 1-bromooctane (29 g, 150 mmol). The solution was heated at 60° C. for 5 hours. The THF was then removed under vacuum, and the resulting material was extracted with pentane (200 ml) with the liquid extract isolated by filtration. The isolated liquid was transferred to a new flask. The isolated liquid was placed under vacuum to remove the pentane and yield the product. Yield=22.65 g (84.5% based on 1-bromooctane).

Sample 4. To a stirring solution of CpMgCl (200 ml, 1.13 M/THF, 226 mmol) was added 1-bromooctane (37.1 g, 192 mmol). The solution was heated at 60° C. for 5.5 hours. Most of the THF was removed under vacuum, and the resulting material was extracted with pentane (125 ml) with the liquid extract isolated by filtration into a new flask. The remaining solid was extracted twice with pentane (100 ml), and the extracts were filtered into the flask with the first pentane extraction. The pentane was removed from the combined extracts under vacuum to yield the product. Yield=31.1 g (91% based on 1-bromooctane. About 5% unreacted 1-bromooctane remained).

$^1$H NMR Spectra were obtained for representative alkyl cyclopentadiene compounds prepared in this example. $^1$H NMR δ 6.47 (m, 1.87H), 6.35 (m, 0.94H), 6.22 (m, 0.94H), 6.18 (m, 0.97H), 5.97 (m, 0.96H), 2.79 (m, 2.10H), 2.69 (m, 2.00H), 2.33-2.28 (m, 4.14H), 1.53 (m, 2.30H), 1.46 (m, 2.47H), 1.23 (m, 24.15H), 0.878 (m, 7.15H).

Example 5

Synthesis of $CpC_{10}H_{21}$

To a stirring solution of CpMgCl (97 ml, 1.00 M/THF, 97 mmol) was added 1-bromodecane (16.1 g, 73 mmol). The solution was heated at 60° C. for 7 hours. The THF was removed under vacuum, and the resulting material was extracted with pentane (100 ml) with the liquid extract isolated by filtration. The isolated liquid was transferred to a new flask. The remaining solid was washed with pentane (30 ml) and filtered. The isolated liquid from the pentane extraction and the liquid from the wash were combined and placed under vacuum for 0.5 hour at 40° C. to remove the pentane and yield the product. Yield=12.4 g (82% based on 1-bromodecane).

$^1$H NMR Spectra were obtained for the alkyl cyclopentadiene compounds prepared in this example. $^1$H NMR (250 MHz) δ 6.47 (m, 1.87H), 6.35 (m, 1.06H), 6.22-6.18 (m, 1.91H), 5.97 (m, 1.03H), 2.79 (m, 2.33H), 2.69 (m, 2.00H), 2.33-2.28 (m, 4.43H), 1.53-1.46 (m, 5.31H), 1.23 (m, 36.71H), 0.878 (m, 8.20H)

Example 6

Synthesis of $CpC_{12}H_{25}$

To a stirring solution of CpMgCl (93 ml, 1.1 M/THF, 102 mmol) was added 1-bromododecane (19.1 g, 76.6 mmol). The solution was heated at 60° C. for 6 hours. The THF was removed under vacuum, and the resulting material was extracted with pentane (100 ml) with the liquid extract isolated by filtration into a new flask. The remaining solid was washed with pentane (30 ml) and filtered. The isolated liquid from the pentane extraction and the liquid from the wash were combined and placed under vacuum for 1.5 hours to remove the pentane and yield the product. Yield=16.4 g (91% based on 1-bromododecane).

$^1$H NMR Spectra were obtained for the alkyl cyclopentadiene compounds prepared in this example. $^1$H NMR ($C_6D_6$) δ 6.47 (m, 1.98H), 6.35 (m, 1.04H), 6.22 (m, 1.05H), 6.18 (m, 1.06H), 5.97 (m, 1.05H), 2.79 (m, 2.32H), 2.69 (m, 2.00H), 2.33-2.28 (m, 4.55H), 1.53 (m, 2.70H), 1.46 (m, 2.67H), 1.23 (m, 50.40H), 0.878 (m, 8.08H).

Example 7

Synthesis of 3-Chloro-Propylcyclopentadiene

To a stirring solution of CpMgCl (100 ml, 1.00 M/THF, 100 mmol) was added 1-chloro-3-iodo-propane (17.4 g, 85.1 mmol). Upon addition of the 1-chloro-3-iodo-propane, the reaction mixture began to reflux and became cloudy after several minutes. The reaction was stirred at room temperature for 3 hours. The THF was then removed under vacuum, and the resulting material was extracted with pentane with the liquid extract isolated by filtration into a new flask. The pentane was then removed under vacuum to yield the product. Yield=6.31 g (52% based on 1-chloro-3-iodo-propane).

$^1$H NMR Spectra were obtained for the alkyl cyclopentadiene compounds prepared in this example. $^1$H NMR (250 MHz) δ 6.38 (m, 0.82H), 6.28 (m, 0.65H), 6.15 (m, 0.99H), 6.04 (m, 0.85H), 5.83 (m, 0.42H), 3.07 (m, 2.87H), 2.70 (m, 0.92H), 2.50 (m, 2.00H), 2.23 (m, 3.21H), 1.60 (m, 3.12H).

Example 8

Synthesis of $CpCH_2CH_2CH_2OC_6H_5$

To a stirring solution of CpMgCl (138 ml, 1.13 M/THF, 156 mmol) was added (3-bromopropoxy)benzene (25.3 g, 118 mmol). The reaction was heated to 60° C. for 4.5 hours. The THF was then removed under vacuum, and the resulting material was extracted with pentane (100 ml) with the liquid extract isolated by filtration into a new flask. The remaining solid was washed with pentane (50 ml) and filtered. The isolated liquid from the pentane extraction and the liquid from the wash were combined and placed under vacuum to remove the pentane and yield the product. Yield=15.9 g (67% based on (3-bromopropoxy)benzene).

$^1$H NMR Spectra were obtained for the alkyl cyclopentadiene compounds prepared in this example. $^1$H NMR δ 7.16-7.12 (m, 6.38 (m, 5.71H), 6.85 (m, 6.77H), 6.41 (m, 1.97H), 6.31 (m, 1.06H), 6.18 (m, 0.86H), 6.12 (m, 0.86H), 5.19 (m, 1.02H), 3.65 (t, 2.81H), 3.62 (t, 2.07H) 2.74 (m, 2.51H), 2.62 (m, 2.00H) 2.39 (m, 4.69H), 1.86 (m, 2.64H), 1.78 (m, 2.25H).

Example 9

Synthesis of $CpCH_2CH_2OC_6H_5$

To a stirring solution of CpMgCl (146 ml, 1.13 M/THF, 166 mmol) was added (2-bromoethoxy)benzene (25.1 g, 125 mmol). The reaction was heated to 60° C. for 4.5 hours. The THF was then removed under vacuum, and the resulting material was extracted with pentane (100 ml) with the liquid extract isolated by filtration into a new flask. The remaining solid was washed with pentane (50 ml) and filtered. The isolated liquid from the pentane extraction and the liquid from the wash were combined and placed under vacuum to remove the pentane and yield the product. Yield=14.8 g (64% based on (3-bromopropoxy)benzene).

$^1$H NMR Spectra were obtained for the alkyl cyclopentadiene compounds prepared in this example. $^1$H NMR δ 7.15-7.10 (m, 4.66H), 6.83 (m, 5.92H), 6.42 (m, 1.46H), 6.28 (m, 0.77H), 6.18 (m, 1.41H), 5.96 (m, 0.74H), 3.84 (t, 2.07H), 3.73 (t, 1.95H), 2.73 (m, 2.00H), 2.68 (m, 3.77H), 2.63 (m, 1.91H).

Example 10

Synthesis of $CpCH_2CH_2CH_2CH_2Cp$

To a stirring solution of CpMgCl (178 ml, 1.13 M/THF, 200 mmol) was added 1,4-dibromobutane (16.72 g, 77.4 mmol). Upon addition of the dibromobutane there was an exotherm to about 45° C. The reaction was heated to 60° C. for 5 hours. The THF was then removed under vacuum, and the resulting material was extracted with pentane (75 ml) with the liquid extract isolated by filtration into a new flask. The remaining solid was washed with pentane (2×50 ml) and filtered. The isolated liquid from the pentane extraction and the liquid from the wash were combined and kept at −15° C. overnight. A small amount of colorless crystalline solid formed. The solution was separated from the solid by decanting and the solution placed under vacuum to remove the pentane and yield the product. Yield=14.1 g (98% based on 1,4-dibromobutane).

$^1$H NMR Spectra were obtained for the alkyl cyclopentadiene compounds prepared in this example. $^1$H NMR δ 6.45 (m, 1.40H), 6.33 (m, 0.72H), 6.20 (m, 0.74H), 6.15 (m, 0.59H), 5.94 (m, 0.74H), 2.78 (m, 0.2.00H), 2.66 (m, 1.54H), 2.35-2.25 (m, 3.78H), 1.60-1.35 (m, 4.77H).

Example 11

Synthesis of $(CpC_5H_{11})_2ZrCl_2$

To a stirring solution of $CpC_5H_{11}$ (2.00 g, 14.7 mmol) in diethyl ether (ca. 30 ml) was added n-butyllithium (5.4 ml, 2.5 M/hexanes, 13.5 mmol). The reaction mixture formed gel during addition of the n-butyllithium. The reaction mixture was stirred at room temperature for 40 minutes. Next, $ZrCl_4$ $(THF)_2$ solid (5.1 g, 13.5 mmol) was added, and the mixture was stirred at room temperature for 2.5 hours. The solvent was removed under vacuum. The resulting material was extracted with warm hexane (ca. 40 ml) and filtered into a new flask. The remaining solid was extracted with warm hexane (2×20 ml), and the liquids isolated by filtration. The combined filtrates were heated to re-dissolve precipitated solid and upon cooling to room temperature a solid precipitated. The solid precipitate was isolated by filtration, washed with cold pentane (ca. 20 ml) and dried under vacuum at room temperature. Yield=0.81 g (25% based on $CpC_5H_{11}$).

$^1$H NMR Spectra were obtained for the bis(n-alkylcyclopentadienyl)zirconiumdichloride prepared in this example. $^1$H NMR δ 5.93 (m, 4.00H), 5.77 (m, 4.02H), 2.64 (m, 4.10H), 1.46 (m, 4.22H), 1.21 (m, 8.62H), 0.84 (t, 6.20H).

Example 12

Synthesis of $(CpC_6H_{13})_2ZrCl_2$

To a stirring solution of $CpC_6H_{13}$ (2.14 g, 14.2 mmol) in diethyl ether (ca. 30 ml) was added n-butyllithium (8.5 ml, 1.6 M/hexanes, 13.6 mmol). The reaction mixture formed gel during addition of the n-butyllithium. The reaction mixture was stirred at room temperature for 30 minutes. Next, $ZrCl_4$ powder (1.57 g, 6.7 mmol) was added, and the mixture was stirred at room temperature for 3 hours. The solvent was removed under vacuum, and the resulting material was extracted with pentane (ca. 200 ml) with the liquid extract isolated by filtration into a new flask. The filtrate was concentrated under vacuum to about 30 ml and cooled to −35° C. for 2 hours. The solid precipitate that formed was isolated by filtration, washed with cold pentane (ca. 15 ml) and dried under vacuum at room temperature for 3 hours. Yield=1.72 g (55% based on $CpC_6H_{13}$).

$^1$H NMR δ 5.95 (m, 4.00H), 5.75 (m, 3.90H), 2.66 (m, 4.19H), 1.47 (m, 3.91H), 1.21 (m, 12.90H), 0.86 (t, 6.43H).

Example 13

Synthesis of $(CpC_7H_{15})_2ZrCl_2$

To a stirring solution of $CpC_7H_{15}$ (2.34 g, 14.2 mmol) in diethyl ether (ca. 100 ml) was added n-butyllithium (8.5 ml, 1.6 M/hexanes, 13.6 mmol). The reaction mixture was stirred at room temperature for 40 minutes. Next, $ZrCl_4$ powder (1.57 g, 6.7 mmol) was added, and the mixture was stirred at room temperature for 3 hours. The solvent was removed under vacuum, and the resulting material was extracted with warm heptane (ca. 100 ml) with the liquid extract isolated by filtration into a new flask. The filtrate was concentrated under vacuum to about 50 ml and cooled to −35° C. to yield a precipitate that was isolated by filtration, washed with cold pentane and dried under vacuum. Yield=0.96 g. A second crop of product was obtained by concentration and cooling of the supernatent. Yield=0.54 g. Combined yield=1.5 g, (46% based on $ZrCl_4$).

$^1$H NMR Spectra were obtained for the bis(n-alkylcyclopentadienyl)zirconiumdichloride prepared in this example.
$^1$H NMR δ 5.94 (m, 4.00H), 5.75 (m, 4.02H), 2.67 (m, 4.20H), 1.49 (m, 4.32H), 1.23 (m, 17.8H), 0.88 (t, 6.52H).

Example 14

Synthesis of $(CpC_8H_{17})_2ZrCl_2$

To a stirring solution of $CpC_8H_{17}$ (2.54 g, 14.2 mmol) in 100 ml of diethyl ether was added 8.5 ml of n-butyllithium (8.5 ml, 1.6 M/hexanes, 13.6 mmol). The reaction mixture formed gel during addition of n-butyllithium. The reaction mixture was stirred at room temperature for 40 minutes. Next, $ZrCl_4$ powder (1.57 g, 6.7 mmol) was added, and the mixture was stirred at room temperature overnight. The ether was then removed under vacuum, and the resulting material was extracted with heptane (about 100 ml) by stirring at 80° C. for 30 minutes with the liquid extract isolated by filtration into a new flask. Upon cooling to room temperature, a precipitate formed. The precipitate was isolated by filtration, washed with pentane (15 ml) and dried under vacuum. Yield=0.77 g. The filtrate from the above mixture was concentrated to 50 ml under vacuum and heated to 80° C. again to dissolve the solid. Next, it was cooled to room temperature and then stored at −35° C. overnight. The solid precipitate that formed was isolated by filtration and washed with pentane (10 ml). Yield=1.25 g. The total yield is 57.5% based on $CpC_8H_{17}$.

$^1$H NMR δ 5.94 (m, 4.00H), 5.75 (m, 4.19H), 2.68 (m, 4.26H), 1.50 (m, 4.36H), 1.24 (m, 24.17H), 0.90 (t, 6.37H).

Example 15

Synthesis of $(CpC_{10}H_{21})_2ZrCl_2$

To a stirring solution of $CpC_{10}H_{21}$ (2.94 g, 14.2 mmol) in 100 ml of diethyl ether was added n-butyllithium (8.5 ml, 1.6M/hexanes, 13.6 mmol). The reaction mixture was stirred at room temperature for 40 minutes. Next, $ZrCl_4$ powder (1.57 g, 6.7 mmol) was added, and the mixture was stirred at room temperature for 2.5 hours. The ether was removed under vacuum, and the resulting material was extracted with heptane (about 100 ml) at 80° C. with the liquid extract isolated by filtration into a new flask. The filtrate was concentrated to about 70 ml at 80° C. and cooled to −35° C. overnight. The solid precipitate that formed was isolated by filtration, washed with pentane (5 ml) and dried under vacuum. Yield=2.47 g (63.4% based on $CpC_{10}H_2$).

$^1$H NMR Spectra were obtained for the bis(n-alkylcyclopentadienyl)zirconiumdichloride prepared in this example.
$^1$H NMR δ 5.95 (m, 4.00H), 5.76 (m, 4.02H), 2.69 (m, 4.02H), 1.51 (m, 4.14H), 1.26 (m, 31.48H), 0.91 (t, 6.57H).

Example 16

Synthesis of $(CpC_{12}H_{25})_2ZrCl_2$

To a stirring solution of $CpC_{12}H_{25}$ (3.34 g, 14.2 mmol) in 100 ml of diethyl ether was added n-butyllithium (8.5 ml, 1.6 M/hexanes, 13.6 mmol). The reaction mixture formed gel during addition of n-butyllithium. The reaction mixture was stirred at room temperature for 40 minutes. Next, $ZrCl_4$ powder (1.57 g, 6.7 mmol) was added, and the mixture was stirred at room temperature for 3 hours. The ether was removed under vacuum, and the resulting material was extracted with heptane (about 100 ml) by stirring at 80° C. for 30 minutes. The liquid extract was isolated by filtration into a new flask and then concentrated under vacuum until a precipitate began to form. The mixture was then heated to 80° C. to dissolve the precipitate, cooled to room temperature and at −35° C. overnight. The solid was isolated by filtration, washed with cold pentane (15 ml) and dried under vacuum. Yield=2.51 g (56% based on $CpC_{12}H_{25}$).

$^1$H NMR Spectra were obtained for the bis(n-alkylcyclopentadienyl)zirconiumdichloride prepared in this example.
$^1$H NMR (250 MHz) δ 5.95 (m, 4.00H), 5.74 (m, 3.85H), 2.70 (m, 4.19H), 1.52 (m, 4.21H), 1.28 (m, 40.02H), 0.91 (t, 6.73H).

Example 17

Synthesis of $(CpC_6H_{13})(CpMe_4H)ZrCl_2$

A solution of n-butyl lithium (80.0 ml, 1.61M/hexanes, 129 mmol) in pentane (50 ml) was added to a stirring solution of $CpC_6H_{13}$ (19.95 g, 133 mmol) in pentane (300 ml) over the course of several minutes resulting in gas evolution and refluxing of the mixture. A thick colorless solid precipitated. After stirring for two hours, the solid was isolated by filtration, washed with pentane (2×50 ml) and then dried under vacuum for 3 hours. Yield=16.7 g of $LiCpC_6H_{13}$ (80%).

To a stirring slurry of $(C_5Me_4H)ZrCl_3$ (26.8 g, 84.1 mmol) in ether (300 ml) was added solid $LiCpC_6H_{13}$ (14.0 g, 84.2 mmol). The reaction mixture was stirred for 3 h at room temperature, and the ether was then removed under vacuum. The resulting solid was extracted with toluene (ca. 400 ml) and filtered into a different flask to give a solution and a solid portion that remained on the filter. The solution was reduced under vacuum to about 25 ml resulting in the formation of solid product. To this slurry, pentane (ca. 100 ml) was added, and the slurry was then cooled to −35° C. The precipitate thus formed was isolated by filtration, washed with pentane (ca. 50 ml) and dried under vacuum. Yield=20.43 g. The solid portion that remained on the filter was extracted with toluene (ca. 200 ml) at 60° C. and filtered into a new flask to give a second solution that was concentrated under vacuum to about 70 ml. Pentane (ca. 50 ml) was then added. After cooling to −35° C., the solid precipitate that formed was isolated by filtration, washed with pentane (ca. 30 ml) and dried under vacuum. Yield=9.89 g. Total yield=30.32 g (83%).

$^1$H NMR Spectra were obtained for the (tetramethylcyclopentadienyl)(n-alkylcyclopentadienyl)zirconiumdichloride prepared in this example. $^1$H NMR δ 5.95 (m, 2.00H), 5.74 (m, 1.99H), 5.25 (s, 0.99H), 2.71 (m, 2.07H), 1.93 (s, 5.88H), 1.73, (s, 6.04H), 1.51 (m, 2.06H), 1.21 (m, 6.21H), 0.86 (t, 3.20H).

Example 18

Synthesis of $(CpC_8H_{17})(CpMe_4H)ZrCl_2$

To a solution of $CpC_8H_{17}$ (31.1 g, 0.174 mol) in ether (ca. 350 ml) was added n-butyl lithium (105 ml, 1.61 M/hexanes, 0.169 mol) in 10 ml aliquots over about 45 minutes. The reaction mixture was stirred over the weekend at room temperature. Next, most of the ether was removed under vacuum and pentane (ca. 500 ml) was added. The slurry was then stirred for 1 hour. The solid was isolated by filtration, washed with pentane (ca. 100 ml) and dried under vacuum. Yield=25.5 g of $LiCpC_8H_{17}$.

To a stirring slurry of $LiCpC_8H_{17}$ (8.416 g, 45.68 mmol) was added solid $(C_5Me_4H)ZrCl_3$ (14.58 g, 45.74 mmol). The reaction mixture was stirred overnight at room temperature. The ether was removed under vacuum, and the resulting yellow solid was extracted with toluene (ca. 400 ml) with the extracted liquid filtered into a different flask to give a clear yellow solution. All but about 40 ml of the toluene was removed from the solution under vacuum and pentane (ca. 120 ml) was added. The resulting solid was isolated by filtration, washed with pentane (ca. 40 ml) and dried under vacuum about 3 hours at room temperature. Yield=14.71 g, (70% based on $LiCpC_8H_{17}$).

$^1$H NMR Spectra were obtained for the (tetramethylcyclopentadienyl)(n-alkylcyclopentadienyl)zirconiumdichloride prepared in this example. $^1$H NMR δ 5.96 (m, 2.00H), 5.74 (m, 2.01H), 5.27 (s, 0.99H), 2.72 (m, 2.17H), 1.92 (s, 6.19H), 1.73, (s, 6.31H), 1.54 (m, 2.16H), 1.24 (m, 11.34H), 0.89 (t, 3.18H).

Example 19

Synthesis of $(CpC_{12}H_{25})(CpMe_4H)ZrCl_2$

To a stirring solution of $CpC_{12}H_{25}$ (0.67 g, 2.8 mmol) in diethyl ether (50 ml) was added n-butyllithium (1.7 ml, 1.6 M/hexanes, 2.7 mmol). The reaction mixture formed gel during addition of n-butyllithium. After the reaction mixture was stirred at room temperature for 30 minutes, solid $(C_5Me_4H)ZrCl_3$ (0.84 g of 1.49 mmol) was added, and the mixture was stirred at room temperature for 3 hours. The ether was removed under vacuum, and the resulting material was extracted with heptane (100 ml) by stirring at 80° C. for 20 minutes. The heptane solution was isolated by filtration, transferred to a new flask and cooled to −35° C. overnight. The resulting solid precipitate was isolated by filtration, washed with cold pentane (10 ml) and dried under vacuum at room temperature for 2 hours. Yield=1.0 g (66%).

$^1$H NMR Spectra were obtained for the (tetramethylcyclopentadienyl)(n-alkylcyclopentadienyl)zirconiumdichloride prepared in this example. $^1$H NMR δ 5.97 (m, 2.00H), 5.75 (m, 1.99H), 5.27 (s, 0.98H), 2.73 (m, 2.09H), 1.92 (s, 5.85H), 1.73, (s, 5.99H), 1.54 (m, 2.14H), 1.29 (m, 19.88H), 0.89 (t, 3.14H).

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. While compositions and methods are described in terms of "comprising," "containing," "having," or "including" various components or steps, the compositions and methods can also "consist essentially of" or "consist of" the various components and steps.

What is claimed is:

1. A method of synthesizing at least one alkyl cyclopentadiene compound, which includes alkyl cyclopentadiene and substituted alkyl derivatives thereof, comprising: contacting at least one cyclopentadienyl anion source which comprises at least one reagent selected from the group consisting of a cyclopentadienyl Grignard reagent, sodium cyclopentadienyl, lithium cyclopentadienyl, potassium cyclopentadienyl, and any combination thereof and at least one alkyl group source which comprises at least one reagent selected from the group consisting of an alkyl halide and an alkyl sulfonate, for 4 to 7 hours at the temperature of 50° C. to 65° C., to form at least one alkyl cyclopentadiene compound; and
   extracting the alkyl cyclopentadiene compound with a hydrocarbon solvent wherein the mole ratio of the alkyl group source to the cyclopentadienyl anion source is in the range of from 0.5:1 to 0.9:1.

2. The method of claim 1 wherein the cyclopentadienyl anion source comprises a cyclopentadienyl Grignard reagent.

3. The method of claim 1 wherein the mole ratio of the alkyl group source to the cyclopentadienyl anion source is in the range of from 0.5:1 to 0.8:1.

4. The method of claim 1 wherein the mole ratio of the alkyl group source to the cyclopentadienyl anion source is 0.75:1.

5. The method of claim 1 wherein the alkyl cyclopentadiene compound comprises a $C_3$ to $C_{12}$ alkyl group.

6. The method of claim 1 wherein the alkyl cyclopentadiene compound comprises an alkyl group substituted with one or more heteroatoms or one or more heteroatom-containing groups.

7. The method of claim 1 wherein the alkyl cyclopentadiene compound comprises a substituted alkyl group, wherein the substituted alkyl group is formed by replacing one or more H atoms with an alkenyl radical, an alkynyl radical, a cycloalkyl radical, an aryl radical, an acyl radical, an aroyl radical, an alkoxy radical, an aryloxy radical, an alkythio radical, a dialkylamino radical, an alkoxycarbonyl radical, an arloxycarbonyl radical, a carbomoyl radical, an alkyl- or dialkyl-carbamoyl radical, an acyloxy radical, an acylamino radical, an aroylamino radical, a straight, branched or cyclic, alkylene radical, or any combination thereof.

8. The method of claim 1 wherein the alkyl cyclopentadiene compound comprises a compound selected from the group consisting of n-propylcyclopentadiene, n-butylcyclopentadiene, n-pentylcyclopentadiene, n-hexylcyclopentadiene, n-heptylcyclopentadiene, n-octylcyclopentadiene, n-nonylcyclopentadiene, n-decylcyclopentadiene, n-dodecyclopentadiene, 3-chloro-propylcyclopentadiene, 4-bromobutylcyclopentadiene, 3-phenoxypropylcyclopentadiene, 2-phenoxyethylcyclopentadiene, and any combination thereof.

9. The method of claim 1 wherein the extracting of the alkyl cyclopentadiene compound comprises adding the hydrocarbon solvent to a reaction mixture comprising the alkyl cyclopentadiene compound, filtering solids from the reaction mixture, and removing the hydrocarbon solvent from the reaction mixture.

10. The method of claim 9 comprising removing a solvent from the reaction mixture prior to the extracting of the alkyl cyclopentadiene compound.

11. The method of claim 9 comprising washing the filtered solids with the hydrocarbon solvent.

12. The method of claim 9 wherein the hydrocarbon solvent comprises pentane.

13. The method of claim 1 further comprising converting the alkyl cyclopentadiene compound to at least one metallocene catalyst compound.

14. The method of claim 13 wherein the conversion comprises:
   reacting the alkyl cyclopentadiene compound with a base to form a cyclopentadiene anion; and
   reacting the cyclopentadiene anion with a metal-containing compound to form the metallocene catalyst compound.

* * * * *